(12) United States Patent
Stride et al.

(10) Patent No.: US 10,864,160 B2
(45) Date of Patent: Dec. 15, 2020

(54) BEVERAGE COMPOSITION COMPRISING NANOENCAPSULATED OXYGEN

(71) Applicant: OXFORD UNIVERSITY INNOVATION LIMITED, Oxford (GB)

(72) Inventors: Eleanor Stride, Oxford (GB); Joshua Owen, Oxford (GB); Ray Averre, Oxford (GB)

(73) Assignee: OXFORD UNIVERSITY INNOVATION LIMITED, Oxfordshire (GB)

( * ) Notice: Subject to any disclaimer, the term of this patent is extended or adjusted under 35 U.S.C. 154(b) by 56 days.

(21) Appl. No.: 15/746,380

(22) PCT Filed: Jul. 12, 2016

(86) PCT No.: PCT/GB2016/052103
§ 371 (c)(1),
(2) Date: Jan. 19, 2018

(87) PCT Pub. No.: WO2017/013397
PCT Pub. Date: Jan. 26, 2017

(65) Prior Publication Data
US 2018/0193260 A1    Jul. 12, 2018

(30) Foreign Application Priority Data
Jul. 20, 2015 (GB) .................................. 1512728.5

(51) Int. Cl.
| | | |
|---|---|---|
| A61K 9/16 | (2006.01) | |
| A61K 9/00 | (2006.01) | |
| A61K 47/10 | (2017.01) | |
| A61K 47/24 | (2006.01) | |
| A61K 9/107 | (2006.01) | |
| A61K 33/00 | (2006.01) | |
| A61P 35/00 | (2006.01) | |
| A61K 47/12 | (2006.01) | |

(52) U.S. Cl.
CPC .......... *A61K 9/0095* (2013.01); *A61K 9/1075* (2013.01); *A61K 33/00* (2013.01); *A61K 47/10* (2013.01); *A61K 47/12* (2013.01); *A61K 47/24* (2013.01); *A61P 35/00* (2018.01)

(58) Field of Classification Search
CPC ....... A61K 9/0087; A61K 9/0095; A61K 9/08
See application file for complete search history.

(56) References Cited

U.S. PATENT DOCUMENTS

| 4,466,442 A * | 8/1984 | Hilmann ............... A61K 49/223 |
|---|---|---|
| | | 600/431 |
| 2004/0225022 A1 | 11/2004 | Desai |
| 2007/0203173 A1* | 8/2007 | Mudumba ............ A61K 31/445 |
| | | 514/291 |
| 2010/0239684 A1* | 9/2010 | Fukui ........................ A23L 2/38 |
| | | 424/500 |
| 2012/0087956 A1 | 4/2012 | Simpkins |
| 2013/0323308 A1 | 12/2013 | Simpkins |
| 2014/0010848 A1* | 1/2014 | Kheir .................... A61K 9/0019 |
| | | 424/400 |

FOREIGN PATENT DOCUMENTS

| CN | 101785566 A | 7/2010 |
|---|---|---|
| CN | 101820893 A | 9/2010 |
| WO | WO2012065060 | 5/2012 |
| WO | WO2014026121 | 2/2014 |

OTHER PUBLICATIONS

Search Report dated Apr. 19, 2016, from corresponding GB Patent Application No. 1512728.5, 5 pages.
International Search Report dated Sep. 23, 2016, from corresponding PCT Patent Application No. PCT/GB2016/052103, 4 pages.
Written Opinion of the International Searching Authority dated Sep. 23, 2016, from corresponding PCT Patent Application No. PCT/GB2016/052103, 10 pages.
Office Action dated Jul. 15, 2020 in Chinese Application No. 2016800427146, 8 pages.

* cited by examiner

*Primary Examiner* — Micah Paul Young
(74) *Attorney, Agent, or Firm* — Lee & Hayes PC; Brett L. Nelson; Thu Nguyen

(57) ABSTRACT

The invention relates to a beverage composition comprising: water; oxygen bubbles; a surfactant in an amount of between about 0.1% (v/v) and about 0.5% (v/v); one or more viscosity modifying agent(s) in an amount of between about 0.5% (v/v) and about 2.5% (v/v); and optionally citric acid in an amount of between about 0.1% (v/v) and about 0.5% (v/v). The invention further relates to compositions, methods of treatment for cancer, the composition for use in treatment of cancer, and the manufacture of the composition.

18 Claims, 4 Drawing Sheets

BEVERAGE COMPOSITION COMPRISING NANOENCAPSULATED OXYGEN

CROSS REFERENCE TO RELATED PATENT APPLICATIONS

This Application claims priority to and is a national phase of PCT/GB2016/052103, filed Jul. 12, 2016, which claims priority to GB 1512728.5, filed Jul. 20, 2015, which are incorporated herein by reference in their entirety.

The invention relates to a beverage composition for oral administration of oxygen, and uses thereof.

As a tumour grows, blood supply to the cancer cells can become inadequate due to poor vasculature supply, leading to low or irregular oxygen delivery and tumour hypoxia. Normally cells would die under hypoxic conditions. However, cancer cells can become adapted to the hypoxic environment by mutation. Such tissue hypoxia is a common feature of solid tumours and the cells in these hypoxic regions can be resistant to both radiotherapy and chemotherapy. There has been an increasing realization that effective anti-cancer therapy could exploit this tissue state to help combat the disease. In particular, one method of exploiting tumour hypoxia in anti-cancer therapy is to deliver oxygen locally to the hypoxic tumour together with chemotherapy, radiotherapy, photodynamic or sonodynamic therapy. Such therapies have been investigated by the intravenous injection of oxygen absorbing liquids (http://www.nuvoxpharma.com). However, such liquids use perfluorocarbons which pose a potential environmental and toxicity risk.

Low oxygen levels in muscle tissue is also recognized as a limiting factor in muscle function, such as muscle endurance and recovery. Therefore, the ability to manage the oxygen levels by delivery of oxygen to muscle tissue would provide an advantage to muscle function, for example in an athlete.

An aim of the present invention is to provide an improved method of oxygen delivery to hypoxic tumours for treatment, or to tissue such as muscle for improved function.

According to a first aspect of the invention, there is provided a beverage composition comprising:
water;
oxygen bubbles;
a surfactant in an amount of between about 0.1% (v/v) and about 0.5% (v/v);
one or more viscosity modifying agent(s) in an amount of between about 0.5% (v/v) and about 2.5% (v/v); and optionally
citric acid in an amount of between about 0.1% (v/v) and about 0.5% (v/v).

The invention advantageously provides a drinkable formulation capable of increased stability of oxygen in suspension compared with existing microbubble formulations (intended for use as artificial respiration aids). This reduces the need for there being a very short period between preparing the drink and consuming it and improves the efficiency with which oxygen can be absorbed from the digestive tract into the blood stream and surrounding tissue. Enabling oral administration (as opposed to intravenous injection) reduces the risk of infection for hospital patients and greatly increases the range of uses of the product for consumer applications. The composition is also suitable for drinking, where the taste and texture are palatable, and it non-toxic, whilst also delivering sufficiently stable oxygen bubbles.

The term "drinkable" used herein is understood to mean that the composition is non-toxic and safe to drink for mammals, such as humans. For example, a drinkable composition may be consumed in reasonable quantities without negative health consequences.

The term "beverage" used herein is understood to mean a liquid composition intended to be consumed as a drink.

Surfactant

The surfactant may be provided in an amount of between about 0.2% (v/v) and about 0.5% (v/v). The surfactant may be provided in an amount of between about 0.2% (v/v) and about 0.4% (v/v). The surfactant may be provided in an amount of between about 0.25% (v/v) and about 0.35% (v/v). In one embodiment the surfactant is provided in an amount of about 0.3% (v/v).

In one embodiment, the surfactant may comprise amphipathic surfactant molecules. The surfactant may comprise phospholipids. In one embodiment, the surfactant consists of, or comprises, lecithin. The lecithin may be purified lecithin, for example by a metal catalyst. The surfactant may comprise phospholipids purified from lecithin. Purified lecitihin may consist of Distearoyl-sn-glycero-3-phosphocholine (DSPC). In one embodiment, the surfactant comprises or consists of Distearoyl-sn-glycero-3-phosphocholine (DSPC). The surfactant may comprise phosphatidylcholine and/or phosphatidylethanolamine. The surfactant may consist of phosphatidylcholine and/or phosphatidylethanolamine. The surfactant may comprise a mixture of phosphatidyl choline, phosphatidyl inositol, phosphatidyl ethanolamine, and phosphatidic acid.

The lecithin may comprise soy-bean derived lecithin. In another embodiment, the lecithin may comprise egg derived lecithin. The lecithin may comprise sunflower oil-derived lecithin.

In one embodiment, soy-bean derived lecithin comprises:
about 33-35% soybean oil;
about 20-21% inositol phosphatides;
about 19-21% phosphatidylcholine;
about 8-20% phosphatidylethanolamine;
about 5-11% other phosphatides;
about 5% free carbohydrates;
about 2-5% sterols; and
about 1% moisture.

Viscosity Modifying Agent

The viscosity modifying agent may comprise or consist of glycerol. In another embodiment, The viscosity modifying agent may comprise or consist of glycyrrhizic acid. The viscosity modifying agent may comprise a viscosity modifying agent selected from glycerol, polypropylene glycol, polyethylene glycol, glycyrrhizic acid or a sugar-based syrup; or combinations thereof. In another embodiment, the viscosity modifying agent may comprise a viscosity modifying agent selected from glycerol, polypropylene glycol, polyethylene glycol, glycyrrhizic acid or a sugar-based syrup; or combinations thereof.

The viscosity modifying agent may be provided in an amount of between about 1% (v/v) and about 2% (v/v). In another embodiment, the viscosity modifying agent may be provided in an amount of between about 1% (v/v) and about 1.5% (v/v). In another embodiment, the viscosity modifying agent may be provided in an amount of about 1.25% (v/v) or 1.3% (v/v).

The percentage amount of viscosity modifying agent provided may be in addition to any viscosity modifying agent present in other components of the composition, e.g. any glycerol in lecithin provided as the surfactant.

Citric Acid

In one embodiment citric acid is provided in an amount of between about 0.1% (v/v) and about 0.5% (v/v). In another embodiment citric acid is provided in an amount of between about 0.2% (v/v) and about 0.4% (v/v). In another embodiment citric acid is provided in an amount of about 0.3% (v/v).

Oxygen

The oxygen bubbles may be encapsulated by the surfactant. In particular, surfactants are characterized by a having a hydrophobic group (their tails) and hydrophilic groups (their heads) which can self-arrange in a solution to encapsulate the oxygen. The oxygen bubbles may be nano-sized. The term "nano-sized" is understood to mean an average size range of between about 1 nm and about 1000 nm in diameter. The nano-sized oxygen bubbles may average less than 1000 nm in diameter. The nano-sized oxygen bubbles may be between about 1 nm and about 1000 nm in diameter. The nano-sized oxygen bubbles may be between about 1 nm and about 1000 nm in diameter in as an average of the population of oxygen bubbles. The nano-sized oxygen bubbles may be between about 10 nm and about 1000 nm in diameter as an average of the population of oxygen bubbles. The nano-sized oxygen bubbles may be between about 1 nm and about 800 nm in diameter as an average of the population of oxygen bubbles. The nano-sized oxygen bubbles may be between about 1 nm and about 500 nm in diameter as an average of the population of oxygen bubbles. The nano-sized oxygen bubbles may be between about 10 nm and about 500 nm in diameter as an average of the population of oxygen bubbles. The nano-sized oxygen bubbles may be between about 100 nm and about 500 nm in diameter as an average of the population of oxygen bubbles. The nano-sized oxygen bubbles may be between about 50 nm and about 200 nm in diameter as an average of the population of oxygen bubbles. The nano-sized oxygen bubbles may be between about 100 nm and about 1000 nm in diameter as an average of the population of oxygen bubbles. The nano-sized oxygen bubbles may be between about 200 nm and about 1000 nm in diameter as an average of the population of oxygen bubbles. The nano-sized oxygen bubbles may be between about 400 nm and about 1000 nm in diameter as an average of the population of oxygen bubbles. The nano-sized oxygen bubbles may be between about 500 nm and about 1000 nm in diameter as an average of the population of oxygen bubbles. The nano-sized oxygen bubbles may be between about 700 nm and about 900 nm in diameter as an average of the population of oxygen bubbles.

In one embodiment, the oxygen is pure oxygen. In another embodiment, the oxygen may be provided in a gas mixture, with another gas or gases. The gas mixture may comprise at least 80% oxygen. Alternatively, the gas mixture may comprise at least 85% oxygen. Alternatively, the gas mixture may comprise at least 90% oxygen. The gas mixture may comprise at least 95% oxygen. In one embodiment, the gas mixture comprises at least 99% oxygen.

The oxygen partial pressure in the composition may be at least 25 relative KPa. In another embodiment, the oxygen partial pressure in the composition may be at least 30 relative KPa. In another embodiment, the oxygen partial pressure in the composition may be at least 32 relative KPa. In another embodiment, the oxygen partial pressure in the composition may be at least 35 relative KPa. In another embodiment, the oxygen partial pressure in the composition may be at least 40 relative KPa. The oxygen partial pressure may be measured under atmospheric pressure at room temperature, or at 37° C.

The composition may not comprise perfluorocarbon. Additionally or alternatively, the composition may not comprise sulphur hexafluoride.

The composition may comprise one or more additional ingredients selected from flavour enhancers, colouring, preservative, fragrance, minerals, and nutrients; or combinations thereof.

The composition may additionally comprise an emulsifier, such as xanthan gum. The xanthan gum may be provided at a concentration of about 2 mg/ml.

In one embodiment, the composition comprises or consists of lecithin as the surfactant; glyzhyrric acid (GA) as the viscosity modifier; and water. The lecithin may be provided at about 1.5 mg/ml, and glyzhyrric acid at about 2.4 mg/ml.

In one embodiment, the composition comprises or consists of lecithin as the surfactant; glyzhyrric acid (GA) as the viscosity modifier; xanthan gum; and water. The lecithin may be provided at about 1.5 mg/ml, glyzhyrric acid at about 2.5 mg/ml, and xanthan gum at about 2 mg/ml.

In one embodiment, the beverage composition may comprise or consist of:
water;
oxygen bubbles;
a surfactant in an amount of about 0.3% (v/v);
one or more viscosity modifying agent(s) in an amount of about 1.25% (v/v); and
citric acid in an amount of about 0.3% (v/v).

According to another aspect of the invention, there is provided a composition for forming a nanoencapsulated oxygen beverage, wherein the composition comprises
water;
surfactant in an amount of between about 0.1% (v/v) and about 0.5% (v/v);
viscosity modifying agent in an amount of between about 0.5% (v/v) and about 2.5% (v/v); and optionally
citric acid in an amount of between about 0.1% (v/v) and about 0.5% (v/v).

In one embodiment, citric acid is provided in an amount of between about 0.1% (v/v) and about 0.5% (v/v).

In one embodiment, the composition for forming a nanoencapsulated oxygen beverage may comprise or consist of:
water;
a surfactant in an amount of about 0.3% (v/v);
one or more viscosity modifying agent(s) in an amount of about 1.25% (v/v); and
citric acid in an amount of about 0.3% (v/v).

According to another aspect of the invention, there is provided a composition for mixing with water and forming a nanoencapsulated oxygen beverage, wherein the composition comprises
surfactant in an amount of between about 0.1% (v/v) and about 0.5% (v/v);
viscosity modifying agent in an amount of between about 0.5% (v/v) and about 2.5% (v/v); and optionally
citric acid in an amount of between about 0.1% (v/v) and about 0.5% (v/v).

In one embodiment, citric acid is provided in an amount of between about 0.1% (v/v) and about 0.5% (v/v).

The composition may be in the form of a paste (e.g. prior to adding water). The composition may be mixed or sparged with oxygen gas. The mixing may be by agitation of the composition in a container with oxygen.

Advantageously, the combination of surfactants and viscosity agents in the invention is capable of producing a suspension of stable oxygen nanoparticles (i.e. in which oxygen is encapsulated) upon agitation or sparging of the composition with oxygen gas. The reduction in surface tension and diffusivity stabilise the oxygen in this form so that it is only released gradually over time.

According to another aspect of the invention, there is provided a method of treating cancer in a subject comprising the oral consumption of a composition according to the invention herein.

According to another aspect of the invention, there is provided use of the composition according to the invention herein for oral consumption to enhance oxygen delivery to muscle.

According to another aspect of the invention, there is provided use of the composition according to the invention herein for oral consumption to enhance athletic and/or muscle performance.

The enhanced athletic performance may comprise enhanced stamina, recovery, strength, reactivity or speed of a muscle performance.

According to another aspect of the invention, there is provided a method of treating cancer in a subject comprising the oral consumption of a composition comprising:
water;
oxygen bubbles;
surfactant in an amount of between about 0.1% (v/v) and about 0.5% (v/v);
viscosity modifying agent in an amount of between about 0.5% (v/v) and about 2.5% (v/v); and optionally
citric acid in an amount of between about 0.1% (v/v) and about 0.5% (v/v).

In one embodiment, citric acid is provided in an amount of between about 0.1% (v/v) and about 0.5% (v/v).

According to another aspect of the invention, there is provided a composition for use in treating cancer in a subject, the composition comprising:
water;
oxygen bubbles;
surfactant in an amount of between about 0.1% (v/v) and about 0.5% (v/v);
viscosity modifying agent in an amount of between about 0.5% (v/v) and about 2.5% (v/v); and optionally
citric acid in an amount of between about 0.1% (v/v) and about 0.5% (v/v).

In one embodiment, citric acid is provided in an amount of between about 0.1% (v/v) and about 0.5% (v/v).

The oral consumption of the composition by the subject may be in combination with an anti-cancer therapy. The anti-cancer therapy and the consumption of composition of the invention may be concurrent or sequential.

The anti-cancer therapy may comprise one or more of chemotherapy, radiotherapy, photodynamic therapy or sonodynamic therapy.

The cancer may comprise a solid tumour cancer. The solid tumour may be characterized by, or susceptible to, tissue hypoxia. The solid tumour may be hypoxic. The skilled person will understand that the level of hypoxia may vary between patients and tissue types. However, is understood to include regions of tissue in which the partial pressure of oxygen is substantially below that typically found in a healthy equivalent tissue. Oxygen content in tissue (e.g. to determine hypoxia) can be measured in a number of ways known to the skilled person. For example a directly implanted probe can measure a change in fluorescence produced by oxygen absorption. Other techniques utilise the change in the colour of blood and hence optical absorption spectrum. For cancer diagnosis in human patients magnetic resonance spectroscopy is typically used. Histological techniques can also be used on biopsy samples to determine hypoxia.

The compositions, methods and use of the invention may provide a sustained increase in oxygen content in a hypoxic tumour following oral administration. The sustained oxygen increase may be over a period of at least 10 minutes. Alternatively, the sustained oxygen increase may be over a period of at least 15 minutes. Alternatively, the sustained oxygen increase may be over a period of at least 20 minutes.

According to another aspect of the invention, there is provided a method of forming a beverage composition for oral administration of oxygen bubbles comprising:
mixing surfactant, viscosity modifying agent, and optionally citric acid, into a volume of liquid, wherein the surfactant is in an amount of between about 0.1% (v/v) and about 0.5% (v/v); the citric acid is in an amount of between about 0.1% (v/v) and about 0.5% (v/v); and the viscosity modifying agent is in an amount of between about 0.5% (v/v) and about 2.5% (v/v); and
packaging the composition into a container comprising oxygen gas.

In one embodiment, the citric acid is provided in the mixture.

The composition and the oxygen gas may be, or arranged to be, separated in the container until required for use.

The surfactant, citric acid and viscosity modifying agent may be pre-mixed into a paste prior to adding it to the volume of water. In another embodiment, the surfactant, citric acid and viscosity modifying agent may be added separately from each other or in combinations.

According to another aspect of the invention, there is provided a method of forming a beverage composition for oral administration of oxygen bubbles comprising:
forming a paste by mixing surfactant, viscosity modifying agent, and optionally citric acid;
packaging the paste in a container, wherein the container comprises oxygen gas; and a volume of liquid, wherein the surfactant is in an amount of between about 0.1% (v/v) and about 0.5% (v/v); the citric acid is in an amount of between about 0.1% (v/v) and about 0.5% (v/v); and the viscosity modifying agent is in an amount of between about 0.5% (v/v) and about 2.5% (v/v).

In one embodiment, the citric acid is provided in the paste mixture.

The paste and volume of liquid may be, or arranged to be, separated in the container until required for use.

In one embodiment, the oxygen is pure oxygen. In another embodiment, the oxygen may be provided in a gas mixture, with another gas or gases. The gas mixture may comprise at least 80% oxygen. Alternatively, the gas mixture may comprise at least 85% oxygen. Alternatively, the gas mixture may comprise at least 90% oxygen. The gas mixture may comprise at least 95% oxygen. In one embodiment, the gas mixture comprises at least 99% oxygen.

The volume of liquid may comprise or consist of water. The water may be distilled water. In one embodiment, the water may be filtered deionized water.

The volume of liquid may be oxygenated by sparging with oxygen, for example prior to packaging.

The method may further comprise the step of agitating the packaged composition to form oxygen bubbles in the composition. The agitation may comprise shaking, for example by hand. The agitation may be for a period of at least 5 seconds. Alternatively, the agitation may be for a period of at least 10 seconds. Alternatively, the agitation may be for a period of at least 20 seconds. Alternatively, the agitation may be for a period of at least 25 seconds. Alternatively, the agitation may be for a period of at least 30 seconds.

The agitation may be immediately prior to drinking. In one embodiment, the agitation is less than 1 minute prior to drinking. In another embodiment, the agitation is less than 5 minutes prior to drinking. In another embodiment, the agitation is less than 10 minutes prior to drinking.

The combined paste and volume of liquid may be stirred prior to packaging to form a homogenous composition. Alternatively, the combined paste and volume of liquid may be stirred to form a homogenous composition prior to agitation.

In one embodiment the composition is sterilised, or at least treated for sterilization or reducing the bio-burden of the composition.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1 shows the stability and level of oxygen held in a sample of the composition according to the invention.

FIG. 2 shows the delivery of oxygen in vivo in a mouse tumour model. FIG. 2A shows the initial change in oxygen levels in the tumour following administration of the drink of the invention. FIG. 2B shows the reading taken at a separate probe position approximately 10 minutes later.

The aim of our formulation is to provide increased stability of oxygen in suspension compared with existing microbubble formulations (intended for use as artificial respiration aids e.g. http://www.ncbi.nlm.nih.gov/pmc/articles/PMC3563146/) and nanobubble waters (http://www.chem1.com/CQ/oxyscams.html). This reduces the need for there being a very short period between preparing the drink and consuming it and improves the efficiency with which oxygen can be absorbed from the digestive tract into the blood stream and surrounding tissue. Enabling oral administration (as opposed to intravenous injection) reduces the risk of infection for hospital patients and greatly increases the range of uses of the product for consumer applications.

It has been demonstrated in the present study that there is a sustained increase (>20 mins) in the oxygen content of a hypoxic tumour following oral delivery, which has not been shown before in other treatment methods. This differs from microbubble formulations that require intravenous injection and have been shown to affect blood oxygen and cardiac tissue oxygen levels.

Example Formulation
  Materials
    100 ml purified water saturated by sparging with oxygen for 2 minutes
    0.3 ml lecithin (soy derivative)
    0.3 ml citric acid powder
    1.25 ml glycerol
Volume ratio can be scaled to required quantity
  Preparation
Lecithin, citric acid and glycerol are combined by stirring to form a liquid paste. Immediately prior to use the paste is added to the purified water in a vessel at least twice the volume of the liquid contained therein. Gentle stirring to dissolve the paste is followed by filling the headspace of the vessel with oxygen and sealing. The vessel is then shaken vigorously for 30 seconds.

In Vitro Measurements

Figure 1:
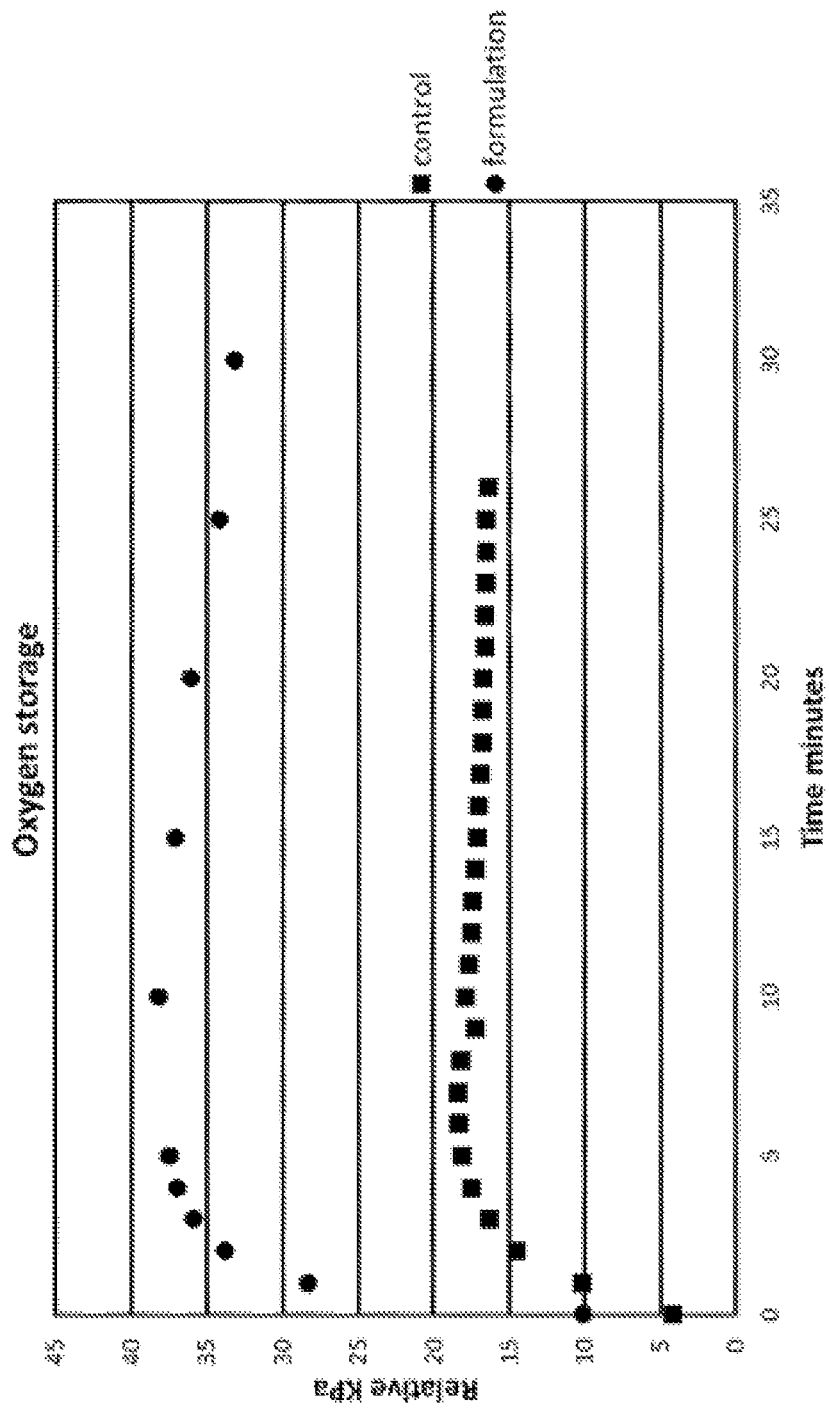

With reference to FIG. 1, a Terumo oxygen meter was used to measure the oxygen content of water before and after addition of 3 ml samples of the above formulation. As a control the measurements were repeated with 3 ml of water that had been sparged with oxygen and shaken but without the addition of any other components. The formulation of the invention demonstrated superior oxygen storage for a period of greater than 25 minutes relative to the control. Repeating the measurements at 37° C. showed a small (~10%) decrease in maximum oxygen partial pressure.

In Vivo Measurements

Figure 2A:
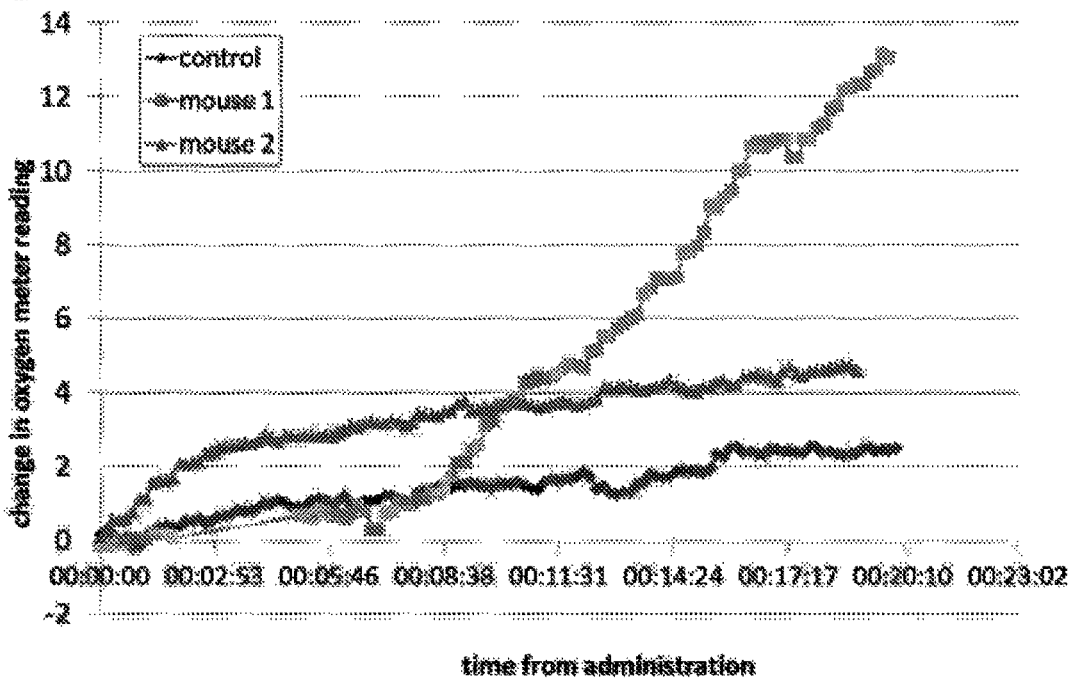
Figure 2B:
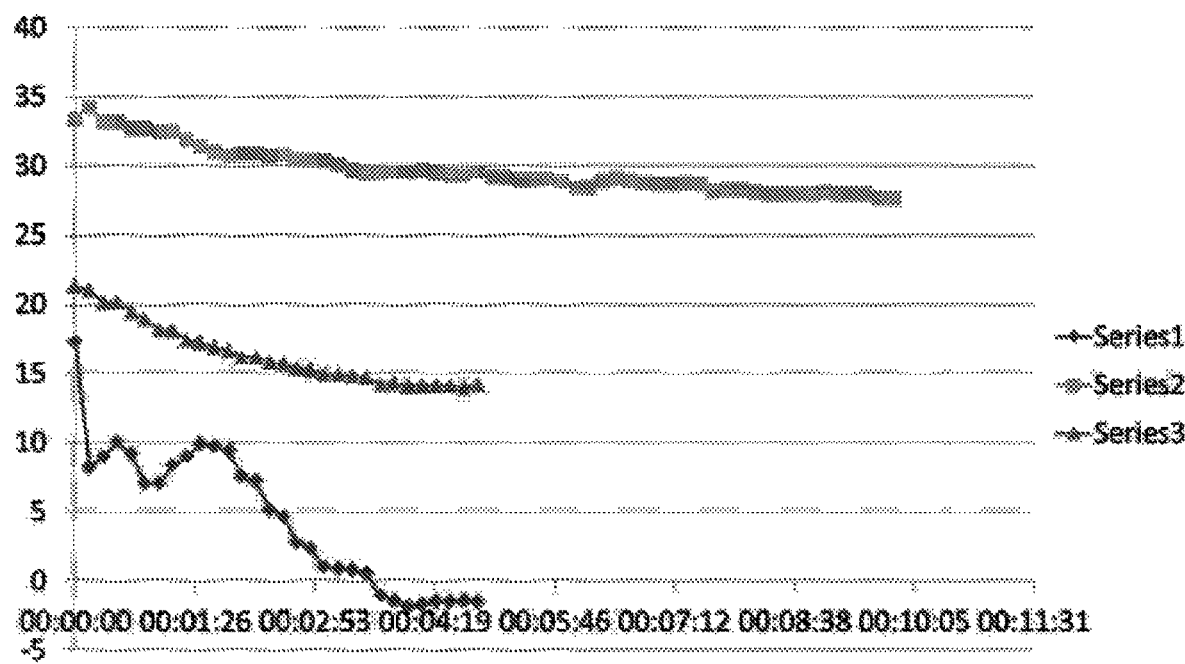
Figure 3:
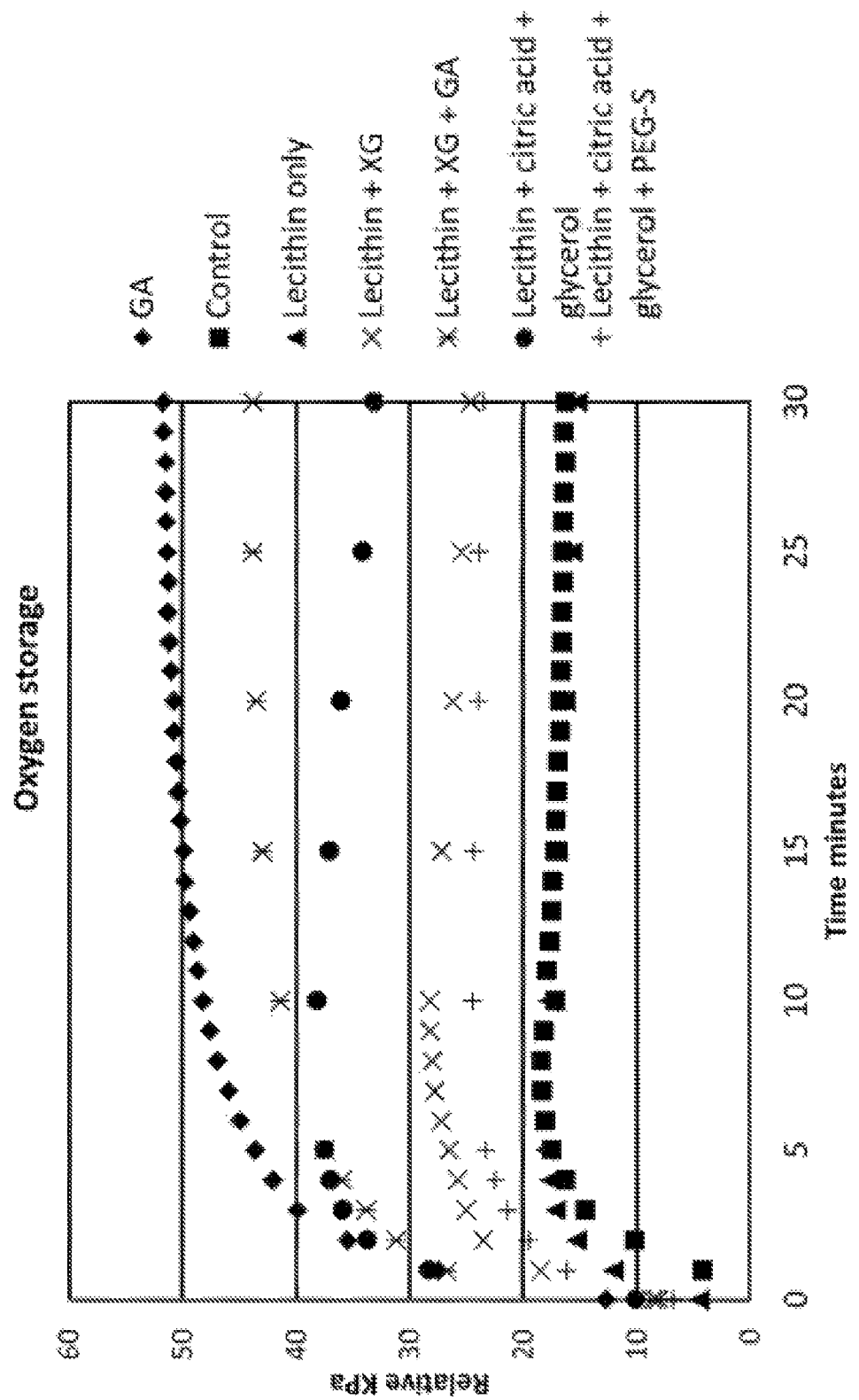
FIG. 3 shows change in oxygen partial pressure with different formulations.
Figure 4:
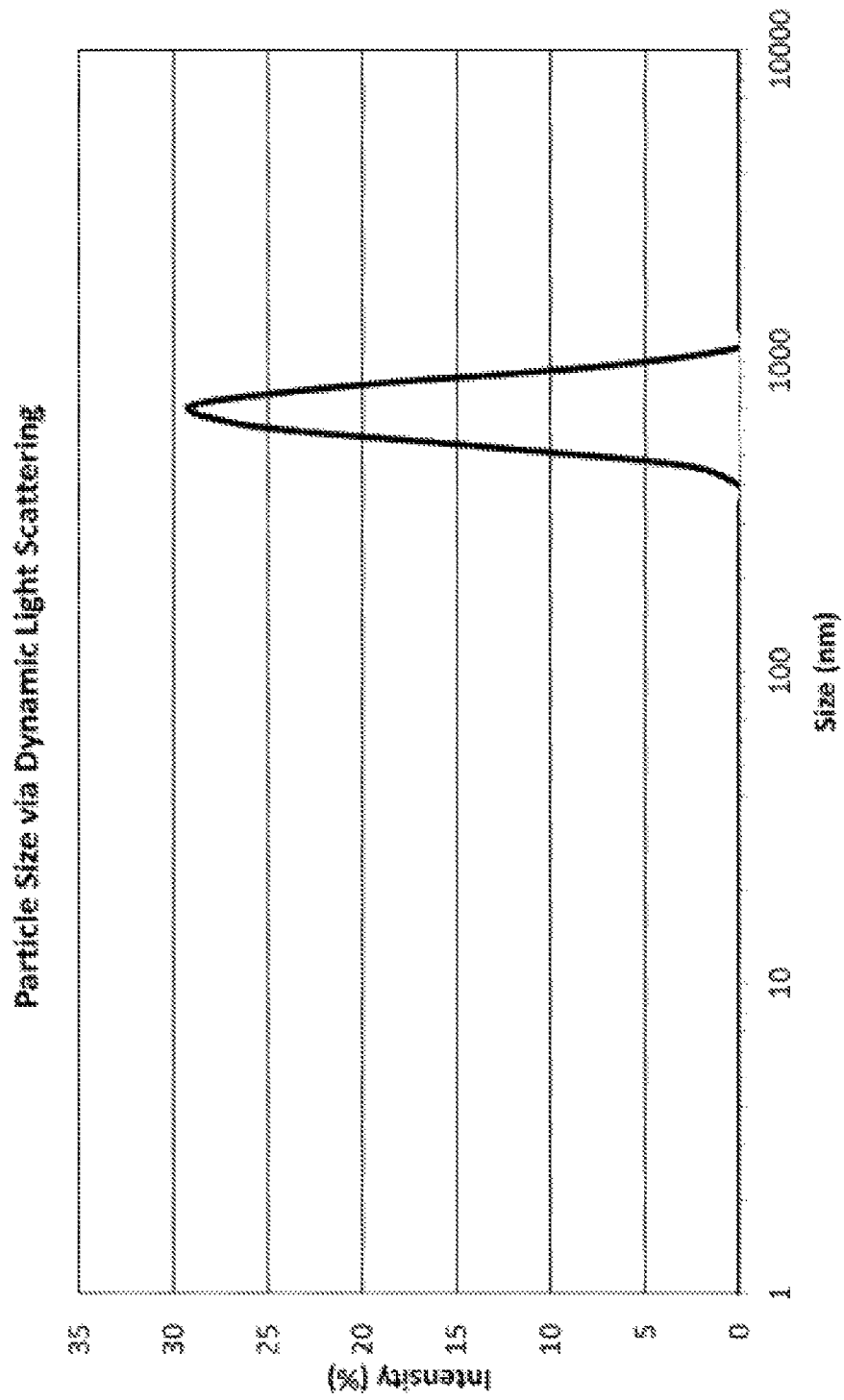
FIG. 4 shows nanobubble sizes in the oxygenated composition of the invention as measured by dynamic light scattering.

With reference to FIGS. 2 and 3, mice bearing hind limb pancreatic tumours were anaesthetized and the formulation (or control) was administered via gavage. An oxygen probe was implanted in the tumour and the change in oxygen level recorded over time.

Each line represents a different mouse. FIG. 2A shows the initial change in oxygen levels in the tumour following administration of the drink of the invention. Mouse 1 was given the fully agitated mixture. Mouse 2 was given the mixture with gentle mixing only. The control mouse was given water treated in the same way but without the addition of the formulation ingredients. FIG. 2B shows the reading taken at a separate probe position approximately 10 minutes later indicating the sustainment of the rise in oxygen levels.

Formulation Optimization

A number of different ingredient combinations were tested, with the reported result the consensus of a panel of 7. Examples are:

(i) Lecithin alone 15 mg in 10 ml.
Result: poor oxygen stabilization (see FIG. 3)

(ii) Lecithin+glycerol+citric acid+polyethylene glycol stearate (PEG-S) (15 mg, 0.06 ml, 20 mg, 15 mg in 5 ml).
PEG-S was expected to act as an emulsifier to encourage the formation of gas stabilizing particles.
Result: poor oxygen stabilization (see FIG. 3).

(iii) Lecithin+xanthum gum (XG) (15 mg, 10 mg in 10 ml.)
Xanthan gum was expected to act as an emulsifier to encourage the formation of gas stabilizing particles.
Result: poor oxygen stabilization (see FIG. 1).

(iv) Lecithin+Glyzhyrric acid (GA) (15 mg, 235 mg in 10 ml)
Glyzhyrric acid (GA) is considered to be a good foam stabilizer and sweetener
Result: unpleasant taste.

(v) Lecithin+glyzhyrric acid+xanthum gum (XG) (15 mg, 25 mg, 20 mg in 10 ml)
This mixture was provided to exploit properties of GA as an excellent foam stabilizer and sweetener but at lower concentration.
Result: unpleasant taste.

Despite the unpleasant taste, these compositions may be considered as useful compositions according to the invention. For example in some applications, such as medicine, the taste may not be an issue.

The ingredients were also tested in different ratios:

(i) Lecithin: citric acid:glycerol:water (90 mg: 20 mg:1 ml:9 ml)
This ratio was attempted to increase the concentration of microbubbles and hence more oxygen
Result: Taste adversely affected by extra lecithin; also microbubbles not so useful for oxygen transport due to fragility.

(ii) Lecithin: citric acid:glycerol:water (15 mg: 200 mg:1 ml:9 ml).

This ratio was attempted to determine the effect on bubble formation—which did increase the microbubble formation.

Result: The taste was too acidic.

(iii) Lecithin: citric acid:glycerol:water (15 mg: 200:5 ml:5 ml).

This ratio was attempted to increase the concentration of microbubbles and hence more oxygen.

Result: the texture was too thick for drinking.

The invention claimed is:

1. A beverage composition comprising:
   water;
   oxygen bubbles, wherein the oxygen bubbles comprise at least 80% oxygen;
   a surfactant in an amount of between about 0.1% (v/v) and about 0.5% (v/v);
   one or more viscosity modifying agent(s) in an amount of between about 0.5% (v/v) and about 2.5% (v/v); and
   citric acid in an amount of between about 0.1% (v/v) and about 0.5% (v/v).

2. The beverage composition according to claim 1, wherein the surfactant is provided in an amount of between about 0.2% (v/v) and about 0.4% (v/v).

3. The beverage composition according to claim 2, wherein the surfactant is provided in an amount of about 0.3% (v/v).

4. The beverage composition according to claim 1, wherein the surfactant comprises lecithin or purified surfactant components thereof.

5. The beverage composition according to claim 1, wherein the surfactant comprises phospholipids purified from lecithin.

6. The beverage composition according to claim 1, wherein the surfactant comprises phosphatidylcholine and/or phosphatidylethanolamine.

7. The beverage composition according to claim 1, wherein the viscosity modifying agent comprises a viscosity modifying agent selected from glycerol, polypropylene glycol, polyethylene glycol, glycyrrhizic acid and a sugar-based syrup; or combinations thereof.

8. The beverage composition according to claim 1, wherein the oxygen bubbles are encapsulated by the surfactant.

9. The beverage composition according to claim 1, wherein the oxygen bubbles are nano-sized oxygen bubbles.

10. The beverage composition according to claim 1, wherein the oxygen is pure oxygen or the oxygen is provided in a gas mixture, with another gas or gases.

11. The beverage composition according to claim 1, wherein an oxygen partial pressure in the composition is at least 25 relative KPa.

12. The beverage composition according to claim 11, wherein the oxygen partial pressure in the composition is at least 35 relative KPa.

13. The beverage composition according to claim 1, wherein the composition does not comprise perfluorocarbon and/or sulphur hexafluoride.

14. The beverage composition according to claim 1, wherein the composition comprises one or more additional ingredients selected from flavour enhancers, colouring, preservative, fragrance, minerals, nutrients; and emulsifier; or combinations thereof.

15. A composition for mixing with water and forming a nanoencapsulated oxygen beverage, wherein the composition comprises
   surfactant in an amount to provide between about 0.1% (v/v) and about 0.5% (v/v) in the nanoencapsulated oxygen beverage;
   viscosity modifying agent in an amount to provide between about 0.5% (v/v) and about 2.5% (v/v) in the nanoencapsulated oxygen beverage, the viscosity modifying agent being selected from the list comprising glycerol, polypropylene glycol, polyethylene glycol, glycyrrhizic acid, or combinations thereof; and
   citric acid in an amount to provide between about 0.1% (v/v) and about 0.5% (v/v) in the nanoencapsulated oxygen beverage; wherein the oxygen is encapsulated in bubbles which comprise at least 80% oxygen.

16. A method of treating cancer in a subject comprising orally administering to the subject a composition comprising:
   water;
   oxygen bubbles, wherein the oxygen bubbles comprise at least 80% oxygen;
   surfactant in an amount of between about 0.1% (v/v) and about 0.5% (v/v);
   viscosity modifying agent in an amount of between about 0.5% (v/v) and about 2.5% (v/v); and
   citric acid in an amount of between about 0.1% (v/v) and about 0.5% (v/v).

17. The method according to claim 16, further comprising administering an anti-cancer therapy.

18. The method according to claim 17, wherein the anti-cancer therapy comprises one or more of chemotherapy, radiotherapy, photodynamic therapy or sonodynamic therapy.

* * * * *